United States Patent
Chae et al.

(10) Patent No.: US 6,955,691 B2
(45) Date of Patent: Oct. 18, 2005

(54) EXPANDABLE INTERFUSION CAGE (75) Inventors: Soo-kyung Chae, Seoul (KR); Jae-ryoun Youn, Seoul (KR); Do-heum Yoon, Seoul (KR); Yong-eun Cho, Seongnam-si (KR); Sang-taek Kim, Seoul (KR); Hyung-sang Park, Seoul (KR)

(73) Assignee: Kyungwon Medical Co., Ltd., Seoul (KR)

( * ) Notice: Subject to any disclaimer, the term of this patent is extended or adjusted under 35 U.S.C. 154(b) by 18 days.

(21) Appl. No.: 10/719,756

(22) Filed: Nov. 21, 2003

(65) Prior Publication Data
US 2005/0113917 A1 May 26, 2005

(51) Int. Cl.⁷ .............................................. A61F 2/44
(52) U.S. Cl. ................................ 623/17.16; 623/17.11
(58) Field of Search ..................... 623/17.11, 17.16, 623/17.15, 16.11; 606/95, 99

(56) References Cited

U.S. PATENT DOCUMENTS

| | | | | |
|---|---|---|---|---|
| 5,554,191 A * | 9/1996 | Lahille et al. | ............ | 623/17.11 |
| 5,665,122 A * | 9/1997 | Kambin | .................... | 623/17.16 |
| 6,117,174 A * | 9/2000 | Nolan | ....................... | 623/17.11 |
| 6,129,763 A * | 10/2000 | Chauvin et al. | .......... | 623/17.11 |
| 6,436,140 B1 * | 8/2002 | Liu et al. | .................. | 623/17.11 |
| 6,443,989 B1 * | 9/2002 | Jackson | .................... | 623/17.15 |
| 6,685,742 B1 * | 2/2004 | Jackson | .................... | 623/17.11 |
| 6,767,350 B1 * | 7/2004 | Lob | ............................. | 606/63 |
| 6,773,460 B2 * | 8/2004 | Jackson | .................... | 623/17.15 |
| 6,821,298 B1 * | 11/2004 | Jackson | .................... | 623/17.15 |
| 6,835,206 B2 * | 12/2004 | Jackson | .................... | 623/17.11 |
| 6,852,129 B2 * | 2/2005 | Gerbec et al. | ........... | 623/17.15 |
| 2002/0045943 A1 * | 4/2002 | Uk | ............................ | 623/17.16 |
| 2002/0143401 A1 * | 10/2002 | Michelson | ............... | 623/17.16 |

FOREIGN PATENT DOCUMENTS

| | | |
|---|---|---|
| EP | 0 637 440 A1 | 2/1995 |
| EP | 0 664 994 A1 | 8/1995 |
| FR | 2 719 763 | 11/1995 |
| WO | 9608205 A1 | 3/1996 |
| WO | 98/10722 | 3/1998 |

* cited by examiner

Primary Examiner—Alvin J. Stewart
(74) Attorney, Agent, or Firm—Michael J. Striker (57) ABSTRACT

An expandable interfusion cage comprising a cage body and a spacer. The cage body includes a seat part which is pierced by an orifice and a branch part which defines therein an inside space and has a plurality of elongate branches integrally formed at their proximal ends with the seat part. An opening is defined between two adjoining branches to communicate with the inside space. The spacer is movably assembled in the inside space of the cage body to expand the cage body radially outward. Inward projections are formed at distal ends, respectively, of the branches to project radially inward toward an axis of the cage body. The inside space of the cage body has substantially a circular or polygonal sectional shape. The spacer is engaged with the inward projections of the branches while expanding the cage body.

2 Claims, 10 Drawing Sheets

EXPANDABLE INTERFUSION CAGE

BACKGROUND OF THE INVENTION

1. Field of the Invention

The present invention relates, in general, to an artificial interfusion implant installed in an intervertebral space created from the removal of a damaged spinal disk, and more particularly, to an expandable interfusion cage, expandable to increase in diameter.

2. Description of the Prior Art

In order to stabilize, for extended periods, fractures of a damaged spinal disk in humans, a fusion can be implemented, in which at least two bones of the spinal column are connected with each other by a bony bridge. In implementing interbody fusion as well known to those skilled in the art, so as to restore a normal spatial relationship, a spinal disk is partially cut, and a bone segment is positioned between adjacent vertebrae in a space already occupied by a disk material, to provide immediate stability through mechanical support. Also, by subsequent permanent cross-conjugation of vertebral bones, long-term stability is provided.

The main application of the invention is to provide implants designed to be slid or inserted from a posterior direction between the confronting faces of two consecutive vertebrae in order to maintain a predetermined distance between them and to restore stability to the spinal column, e.g. after a failure of the corresponding joint, by fixing the two vertebrae together.

Several techniques are known at present for restoring a normal lumbar lordosis in this way, by implanting either a graft which in time fuses the vertebrae together, or a prosthesis which fixes them together immediately, while maintaining the possibility of achieving a fusion between the vertebrae in times.

In the second above-mentioned technique, use is made mainly of implants, also known as "cages", some of which are hollow, rigid, and contain only one piece, with inside/outside intercommunication slots for receiving a bone graft which, via said slots, subsequently fuses with the adjacent vertebrae on either side. In this field, reference can be made to International Patent Publication No. WO 96/08205 published on Mar. 21, 1996 for an "Intervertebral fusion cage of conical shape", and European Patent Publication No. EP 637 440 published on Feb. 8, 1995 for an "Intersomatic implant for the spinal column". Nevertheless, cages of those types are of outside dimensions that are given and fixed, whereas the distances between pairs of vertebrae are not constant. In addition, the inclinations of the facing vertebral faces to which a given angular position is to be imparted do not enable rigid cages to be used from a posterior direction. That is, they can be inserted only from an anterior direction.

As a result, other types of cages have been developed with two substantially parallel branches connected to a rigid body through which it is possible to turn a worm screw system which then moves a wedge in a screw engagement on a worm screw from an initial position close to the distal ends of the branches towards the body linking the branches together, thereby splaying the two branches apart angularly. It is then possible to insert such a cage, in an initially flat shape, between the vertebrae, and then by turning the drive axis of the wedge, the desired angle between the branches is adjusted or set from a posterior access.

Such cages or implants are described, for example, in European Patent Publication No. EP 664 994 published on Aug. 2, 1995, entitled "Vertebral intersomatic cage" or in France Patent Publication No. 2 719 763 published on Nov. 17, 1995, entitled "Vertebral implant".

However, such devices which are more mechanical than hollow and rigid cages, and therefore more complex, leave a smaller inside volume for the fusion graft, and because of their flat shape which is not circularly symmetrical, even though they are better at ensuring a given bearing angle between the vertebrae, they require a passage of the same rectangular section to be prepared to receive them, which complicates implementation.

The problem posed is thus to be able to have implants or cages available making it possible simultaneously to ally the shape of a conventional rigid cage, firstly to facilitate implantation and secondly to provide a larger inside volume, with the possibility of increasing the diameter of the distal end of the cage to a given value relative to its end situated adjacent to its point of surgical insertion, after it has been put into place, and corresponding to the posterior face of the vertebrae, while having as few mechanical elements as possible.

Figure 1:
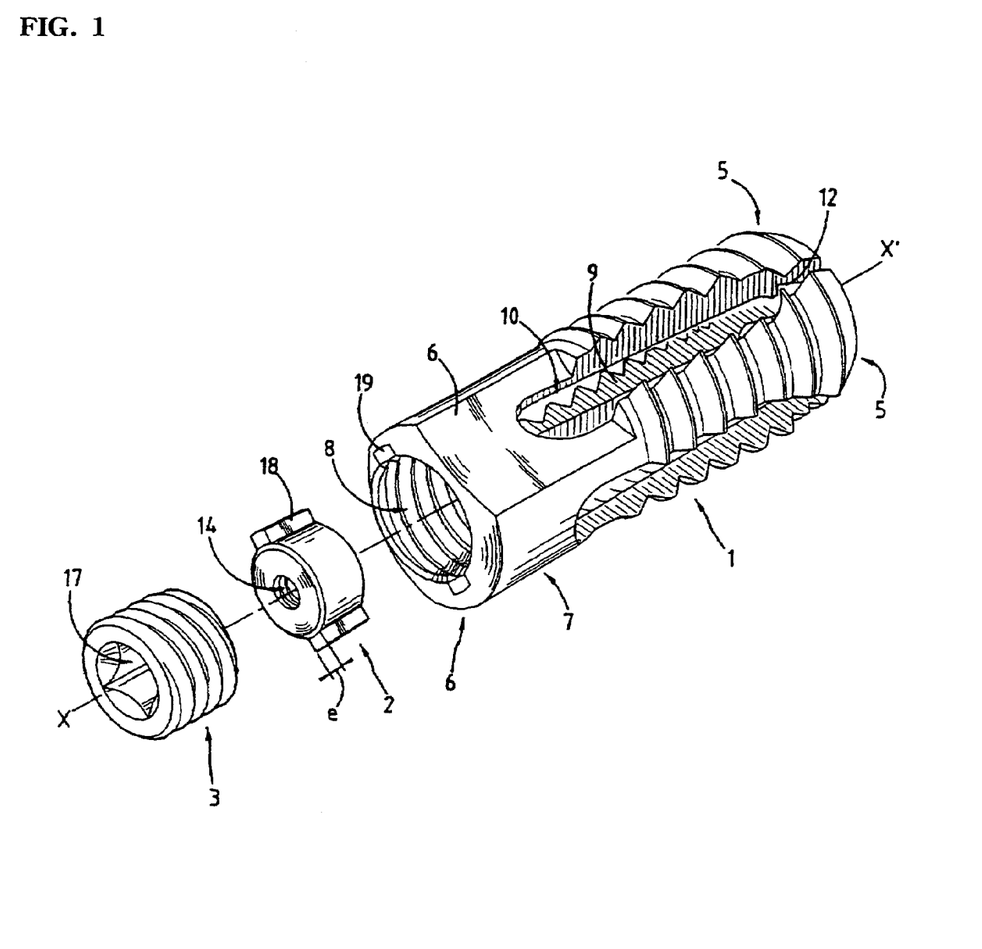
FIG. 1 is an exploded perspective view illustrating a conventional expandable interfusion cage.
Figure 2:
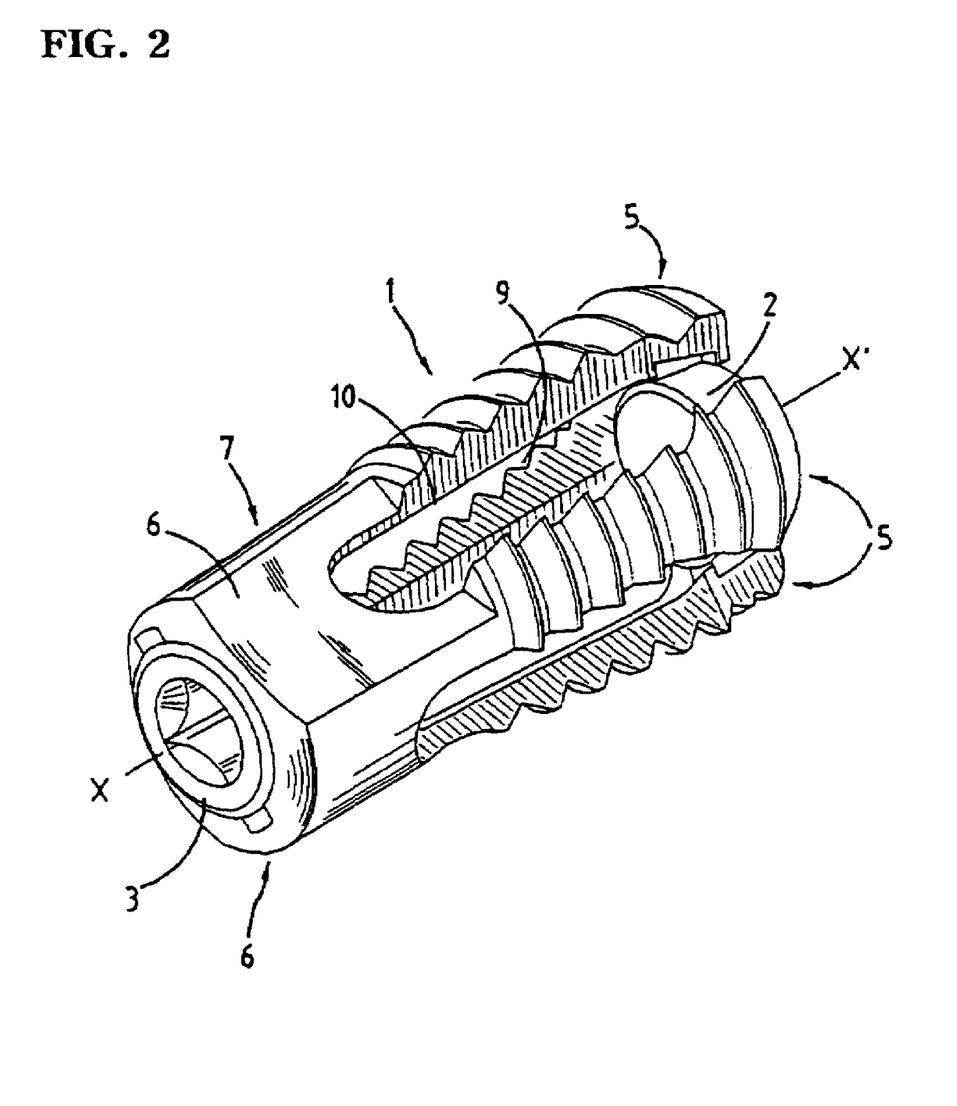
FIG. 2 is a perspective view illustrating an assembled state of the conventional expandable interfusion cage.

In an effort to address this problem, an expandable osteosynthesis cage is disclosed in International Publication No. WO 1998/10722 dated Mar. 19, 1998. In this regard, referring to FIGS. 1 and 2, the cage 1 has a hollow shape and includes a seat 7 and branches 5. The seat 7 serves as a cylindrical body and is pierced by an orifice 8. Each of the branches 5 is connected at one end thereof to the seat 7. A spacer 2 is movably assembled in an inside volume 9, that is, an inside space, of the cage 1. As the spacer 2 is moved toward the distal ends of the branches 5, the branches 5 are biased radially outward by the spacer 2 and thereby expanded.

The expandable osteosynthesis cage partially solves the defects occurring in the conventional art, but some of the defects still remain. In particular, while the spacer 2 is movably assembled in the inside space having a tapered section, if the spacer 2 is moved to the distal ends of the branches 5 to bias radially outward the branches 5, positioning of the spacer 2 at the distal ends of the branches 5 is structurally unstable. Therefore, after the installation of the expandable osteosynthesis cage is completed, the spacer 2 is likely to be unintentionally pushed inward into the inside volume 9 of the cage 1. Further, as can be readily seen from FIG. 2, because an inner surface of each branch 5 is tapered so that a thickness of each branch 5 is increased toward the distal end thereof, when the spacer 2 is moved to the distal ends of the branches 5 to expand them radially outward, limitations exist in increasing the expansion of the branches 5.

SUMMARY OF THE INVENTION

Accordingly, the present invention has been made keeping in mind the above problems occurring in the prior art, and an object of the present invention is to provide an expandable interfusion cage wherein a spacer for expanding a branch part is structured to be moved in an easy manner when it is moved to expand the branch part, structural stability of the expanded branch part is improved, and the expansion of the branch part is increased.

In order to achieve the above object, according to the present invention, there is provided an expandable interfusion cage comprising a cage body of a quadrangular or cylindrical shape and a spacer, the cage body including a seat part which is pierced by an orifice and a branch part which defines therein an inside space and has a plurality of elongate branches integrally formed at their proximal ends with the seat part, with an opening defined between two adjoining branches to communicate with the inside space, the spacer being movably assembled in the inside space of the cage body to expand the cage body radially outward, wherein inward projections are formed at distal ends, respectively, of the branches constituting the branch part to project radially inward toward an axis of the cage body, the inside space of the cage body has substantially a circular or polygonal sectional shape, and the spacer is engaged with the inward projections of the branches while expanding the cage body.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Reference will now be made in greater detail to a preferred embodiment of the invention, an example of which is illustrated in the accompanying drawings. Wherever possible, the same reference numerals will be used throughout the drawings and the description to refer to the same or like parts.

Figure 3:
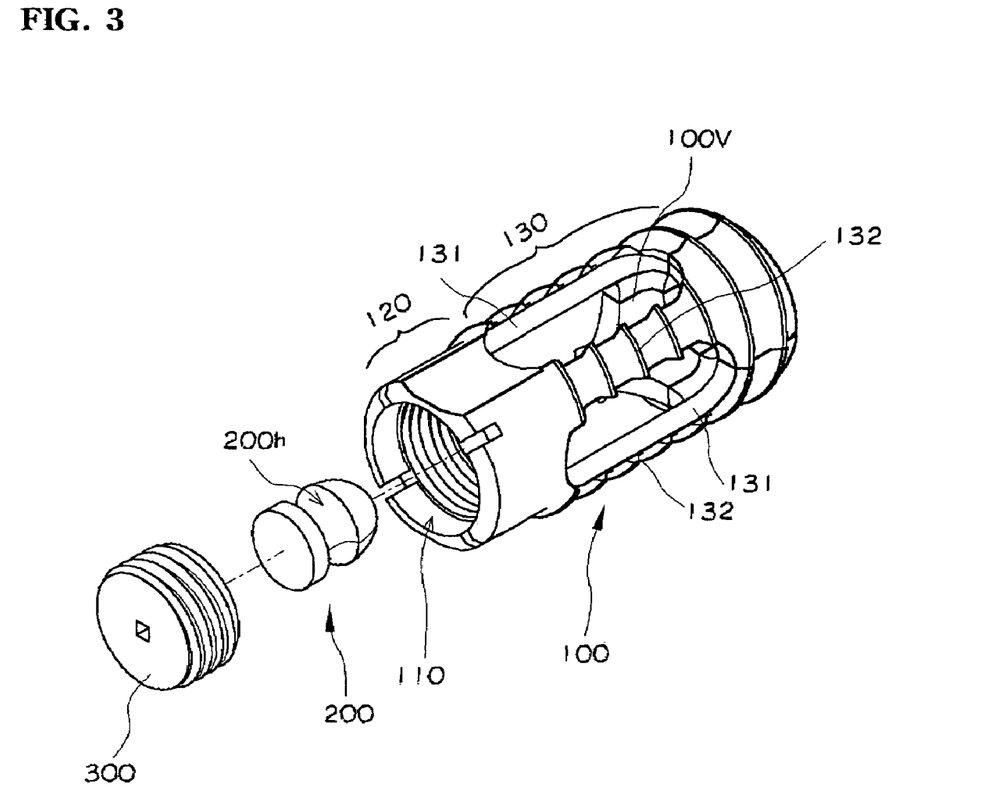
FIG. 3 is an exploded perspective view illustrating an expandable interfusion cage in accordance with a first embodiment of the present invention.
Figure 4:
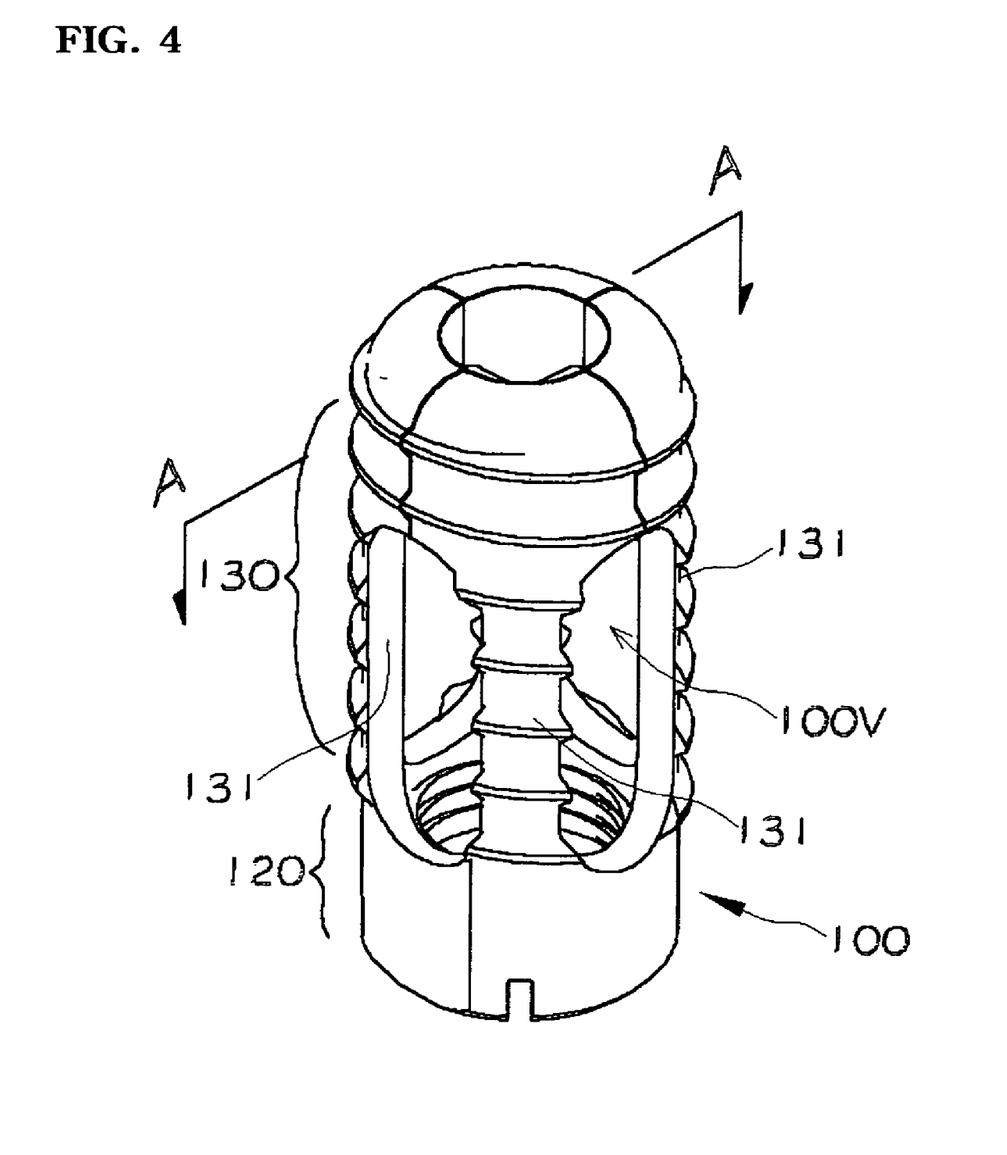
FIG. 4 is a perspective view illustrating an assembled state of the expandable interfusion cage according to the first embodiment of the present invention.
Figure 5:
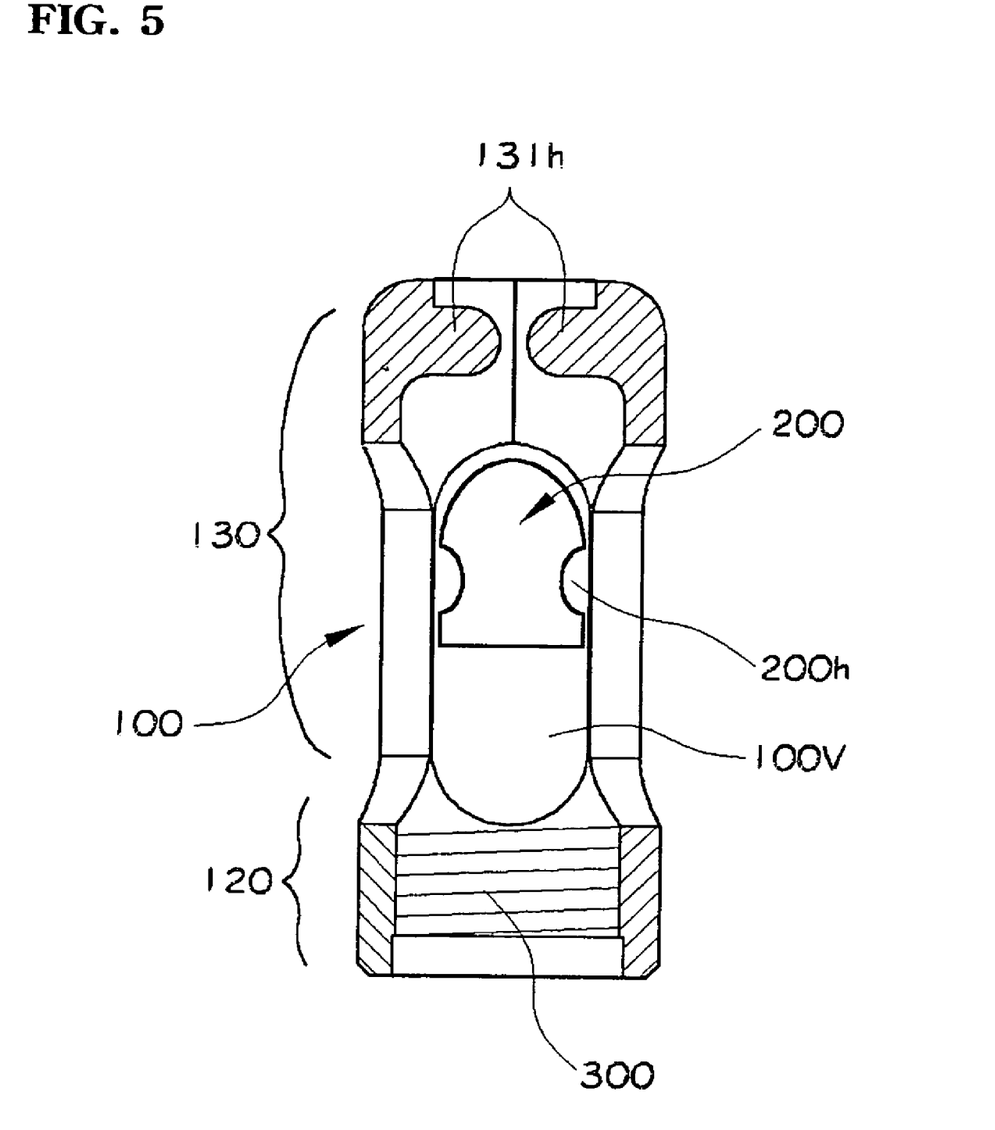
FIG. 5 is a cross-sectional view taken along the line A—A of FIG. 4.
Figure 6:
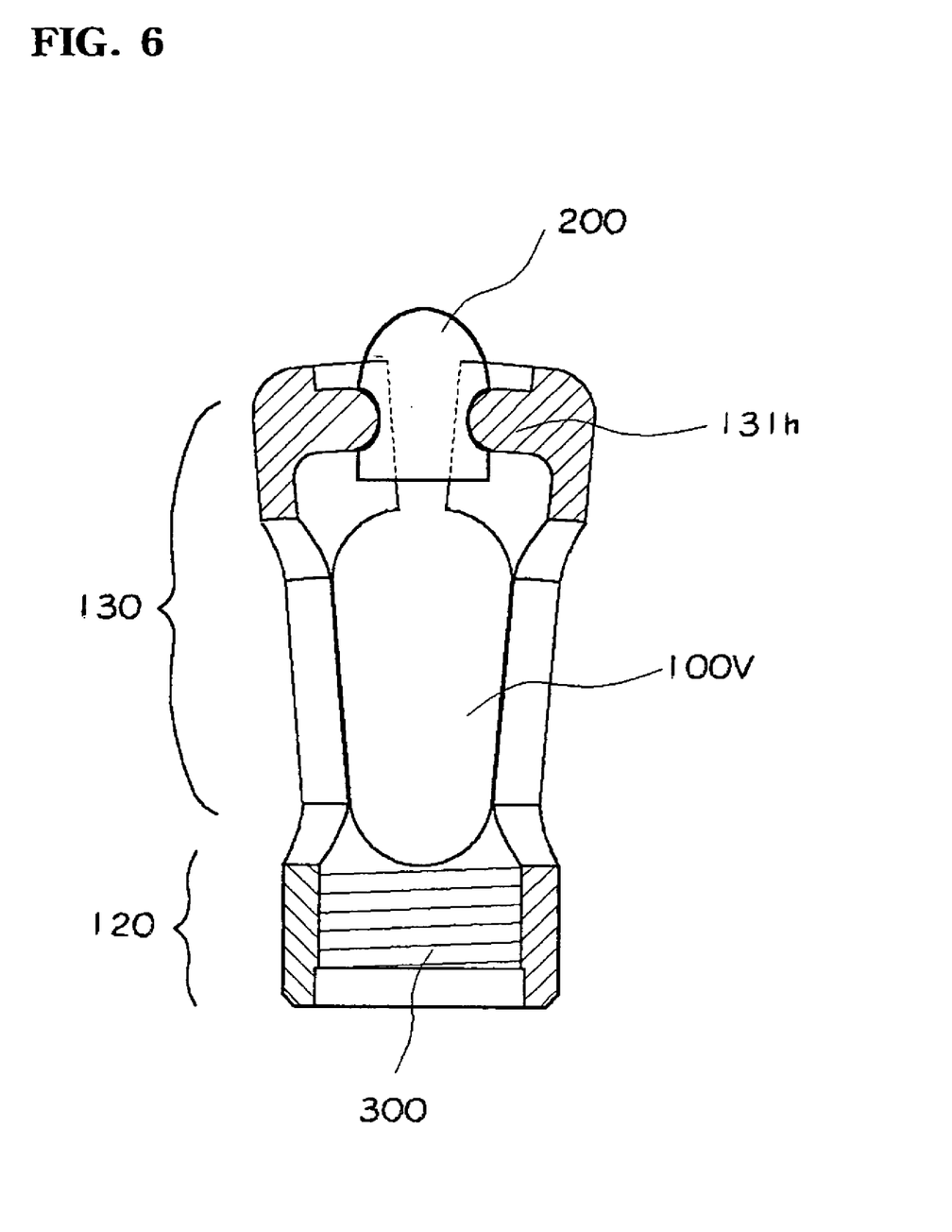
FIG. 6 is a cross-sectional view illustrating an operating state of the expandable interfusion cage according to the first embodiment of the present invention.

FIG. 3 is an exploded perspective view illustrating an expandable interfusion cage in accordance with a first embodiment of the present invention; FIG. 4 is a perspective view illustrating an assembled state of the expandable interfusion cage according to the first embodiment of the present invention; FIG. 5 is a cross-sectional view taken along the line A—A of FIG. 4; and FIG. 6 is a cross-sectional view illustrating an operating state of the expandable interfusion cage according to the first embodiment of the present invention.

Figure 7:
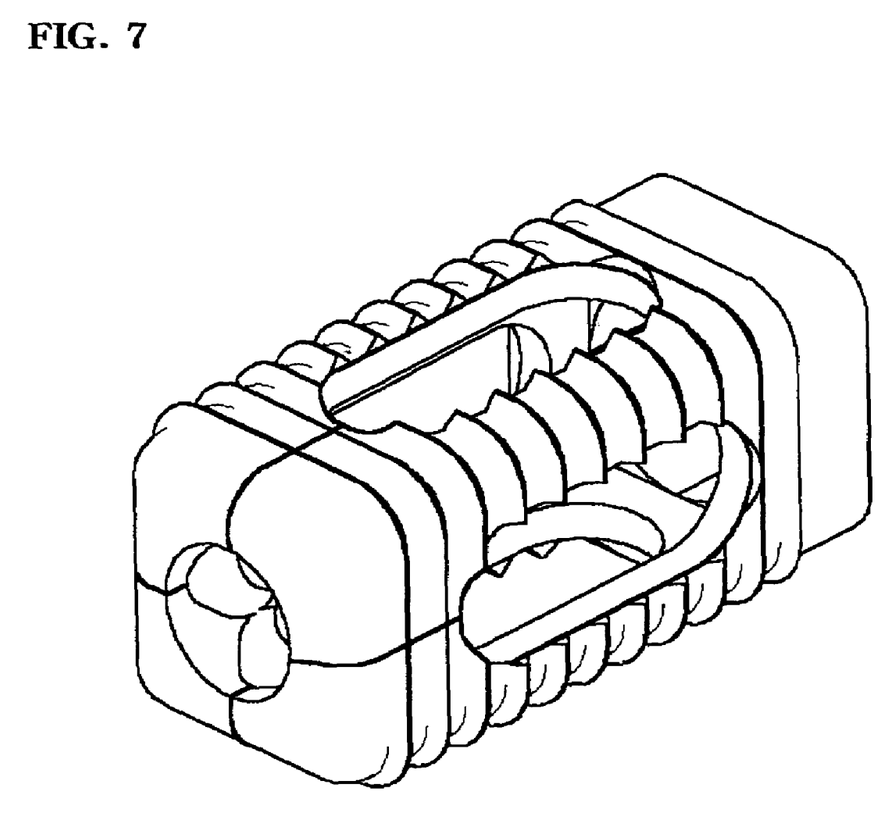
FIG. 7 is a perspective view illustrating an assembled state of a variation of the expandable interfusion cage according to the first embodiment of the present invention.

As shown in FIGS. 3 through 6, an expandable interfusion cage according to the present invention comprises a cage body 100, a spacer 200 and a plug 300. The cage body 100 may be formed to have a quadrangular or cylindrical shape as shown in FIG. 7 or 3, respectively. The cage body 100 is composed of a seat part 120 and a branch part 130. As best shown in FIG. 3, the seat part 120 is pierced by an orifice 110 in which the plug 300 is threadedly assembled. A plurality of branches 131 constituting the branch part 130 are integrally formed at their proximal ends with the seat part 120.

When viewed as a whole, the cage body 100 constructed as mentioned above has a cylindrical shape, so that it defines therein an inside space 100$v$ in which the spacer 200 is received and movably assembled.

Opposite outer surface portions of the seat part 120 constituting the cage body 100 are flattened, and a plurality of triangular valley portions are defined on upper and lower surfaces of the branches 131 of the branch part 130 to produce fixing portions 132. An opening is defined between two adjoining branches 131 constituting the branch part 130 so that the branches 131 can be expanded radially outward as the spacer 200 is moved in the inside space 100$v$.

Inward projections 131$h$ are formed at the distal ends, respectively, of the branches 131 constituting the branch part 130 to project radially inward toward an axis of the cage body 100. Consequently, the inward projections 131$h$ of the branches 131 cooperatively form an end of the cage body 100. That is to say, at the end of the cage body 100, which is opposite to the seat part 120, as shown in FIG. 5, the inward projections 131$h$ of the branches 131 radially extend toward the axis of the cage body 100.

As can be readily seen from FIGS. 3 and 5, the spacer 200 is inserted and movably assembled in the inside space 100$v$ of the cage body 100. The spacer 200 has a head portion which possesses a bullet-shaped configuration and a base portion which possesses a disk-shaped configuration. The spacer 200 is defined with an annular groove 200$h$ between the head portion and the base portion.

In the expandable interfusion cage according to the present invention, constructed as mentioned above, as shown in FIG. 6, as the spacer 200 is inserted into the inside space 100$v$ of the cage body 100 and then moved toward the distal ends of the branches 131 of the branch part 130, the inward projections 131$h$ formed at the distal ends of the branches 131 are engaged into the annular groove 200$h$ of the spacer 200 to be fixedly maintained therein. At this time, as the inward projections 131$h$ are biased radially outward by the spacer 200, the expandable interfusion cage of the present invention is expanded.

Figure 8A:
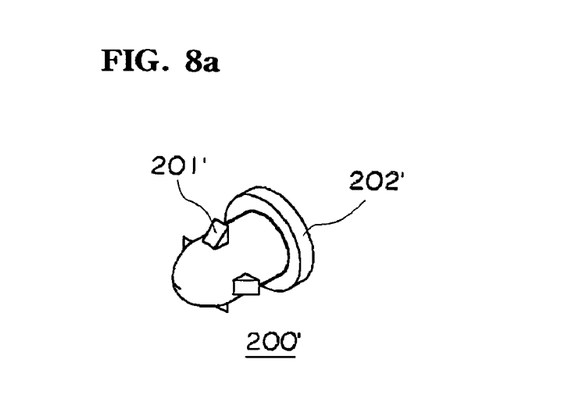
FIGS. 8a through 8c are perspective views illustrating variations of a spacer used in the expandable interfusion cage according to the present invention.
Figure 8B:
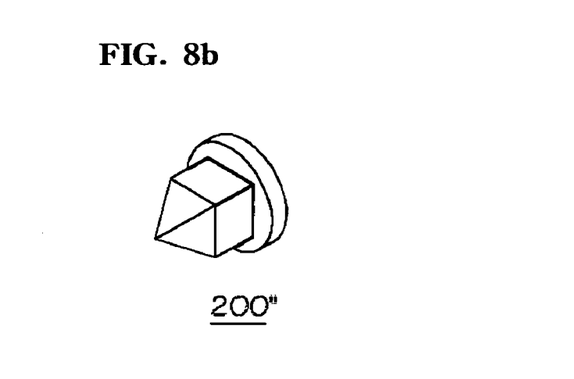
Figure 8C:
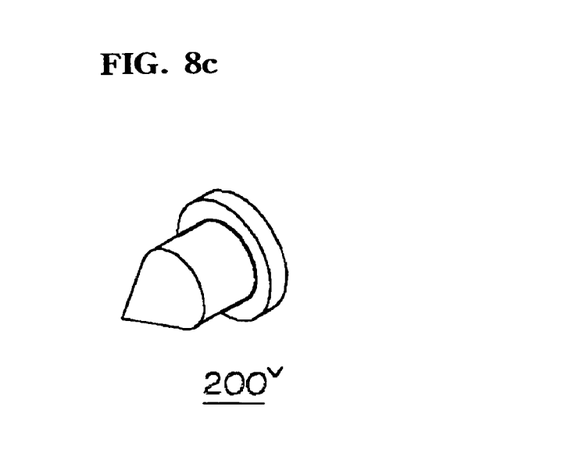

FIGS. 8a through 8c are perspective views illustrating variations of a spacer used in the expandable interfusion cage according to the present invention. Referring to FIG. 8a, a spacer 200' has a head portion which possesses a bullet-shaped configuration and a base portion which is formed to serve as an engaging plate 202' possessing a diameter larger than that of the head portion. A plurality of engaging protuberances 201' each having a downwardly inclined face are formed on an outer surface of the spacer 200' directly below the head portion to be spaced apart one from another in a circumferential direction, in a manner such that the inward projections 131$h$ formed at the distal ends of the respective branches 131 are engaged between the engaging plate 202' and the engaging protuberances 201' while expanding the cage body 100 radially outward. FIG. 8b illustrates a spacer 200'' which has a quadrangular pyramid-shaped head portion, and FIG. 8c illustrates a spacer 200$v$ which has a conical head portion.

In the first embodiment of the present invention, although it was explained that the cage body has a shape of a hexahedron, a person skilled in the art will readily recognize that the cage body may have a cylindrical or a hexagonal shape while not departing from the scope of the present invention.

Also, in the first embodiment of the present invention, while it was explained that the branch part 130 comprises four branches 131, a person skilled in the art will readily recognize that the number of branches is not limited to this and instead six or eight branches can be used to constitute the branch part.

After the expandable interfusion of the present invention is inserted and implanted in an intervertebral space of the spinal column of the human body, powdered bone fills the space between the vertebrae. A powdered-bone leakage prevention door may be provided to prevent the powdered bone from leaking between the vertebrae.

Figure 9:
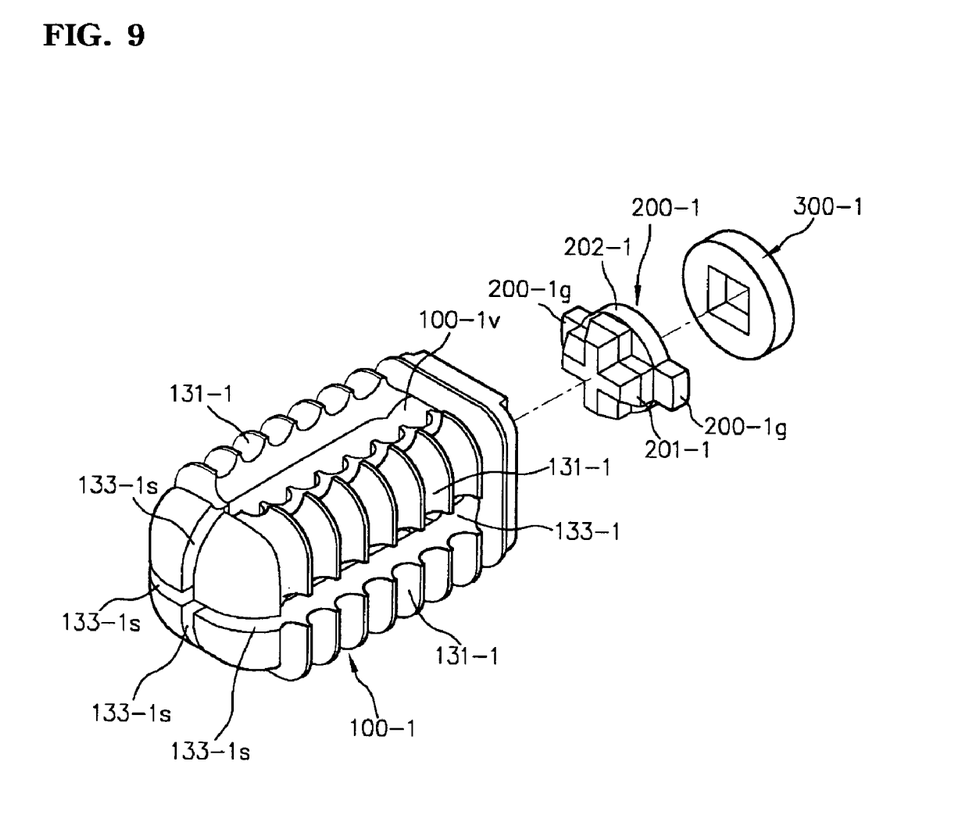
FIG. 9 is an exploded perspective view illustrating an expandable interfusion cage in accordance with a second embodiment of the present invention.

FIG. 9 is an exploded perspective view illustrating an expandable interfusion cage in accordance with a second embodiment of the present invention.

As shown in FIG. 9, in an expandable interfusion cage in accordance with a second embodiment of the present invention, as in the of the first embodiment, a cage body 100-1 defines therein an inside space 100-1$v$, and a branch part comprises four elongate branches 131-1. However, the cage body 100-1 of this second embodiment is differentiated from the cage body 100 of the first embodiment in that a guiding slit 133-1$s$ communicated with an opening 133-1 is defined between two adjoining branches 131-1 when viewed on distal end surfaces of the branches 131-1 so that four guiding slits 133-1$s$ cooperate to create a cross-shaped space.

In this second embodiment of the present invention, a spacer 200-1 comprises a substantially cylindrical spacer body having a head portion 201-1 which is formed as a cross-shaped protrusion of a predetermined size to bias the branches 131-1 radially outward, and a base portion 202-1 which is formed as a disk possessing a diameter larger than that of the head portion 201-1 and has a pair of guide pieces 200-1$g$ oppositely formed at both sides thereof, respectively.

Figure 10:
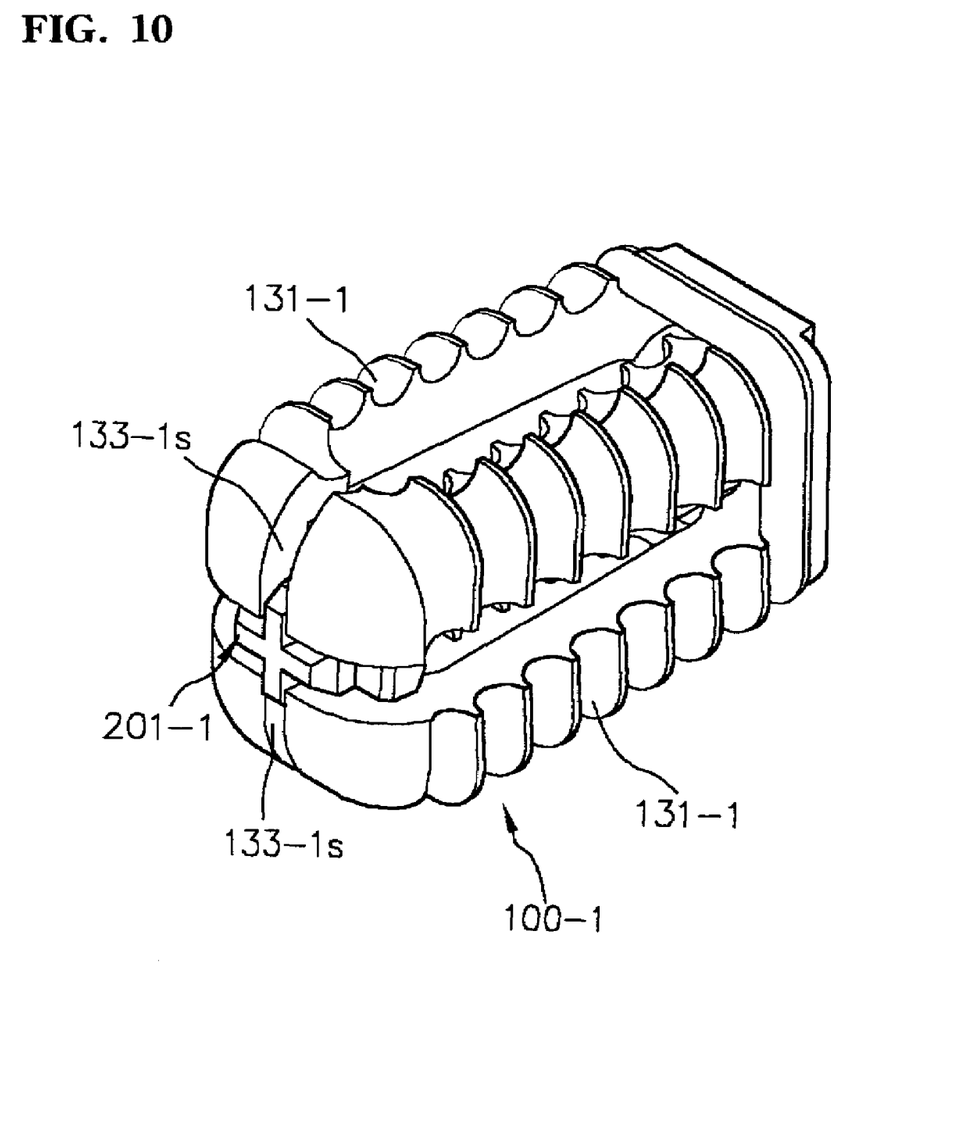
FIG. 10 is a perspective view illustrating an active position of the expandable interfusion cage according to the second embodiment of the present invention.

An expanded state of the cage according to this second embodiment of the present invention, constructed as mentioned above, is illustrated in FIG. 10. As shown in FIG. 10, in the cage according to this second embodiment of the present invention, the spacer 200-1 is movably assembled in the inside space 100-1$v$ which is defined in the cage body 100-1. Then, as the guide pieces 200-1$g$ are moved toward the distal ends of the branches 130-1 to be engaged in two guiding slits 133-1$s$ when viewed at an end of the cage body 100-1 which is opposite to a seat part, the spacer 200-1 biases the branches 130-1 radially outward to allow the cross-shaped head portion 201-1 to expand the cage body 100-1.

As apparent from the above description, the expandable interfusion cage according to the present invention, constructed as mentioned above, provides advantages in that, with the cage implanted in the spinal column of the human body, when a spacer is moved within an inside space of a cage body, inward projections formed at distal ends of branches constituting a branch part are stably engaged in an annular groove of the spacer while expanding the branch part radially outward.

FIG. 10 is a perspective view illustrating an active position of the expandable interfusion cage according to the second embodiment of the present invention. As can be readily seen from the drawing, even though a substantial load is downwardly applied when the cage is inserted into a vertebra, an expanded state of the cage is stably maintained.

In the second embodiment of the present invention, movement of the cage for biasing the inward projections radially outward to expand the cage body is more stably implemented, by which an expanded state of the cage body can be reliably maintained.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An expandable interfusion cage, comprising a cage body including a seat part provided with an orifice and a branch part defining an inside space and having a plurality of elongate branches formed at their proximal ends integrally with said seat part, with each two of said adjoining branches defining therebetween an opening which communicates with said inside space, said branch part having a guiding slit communicating with said opening and defined between each two of said adjoining branches when viewed on distal end surfaces of said branches, so that four said guiding slits are formed and cooperate to create a cross-shaped space; and a spacer movably arranged in said inside space of said cage body and having a substantially cylindrical spacer body with a head portion which is formed as a cross-shaped protrusion biasing said branches radially outwardly, and a base portion formed as a disc with a diameter larger than a diameter of said head portion and having a pair of guide pieces oppositely formed at both sides of said disc and engaging in said guiding slits.

2. An expandable interfusion cage as defined in claim 1, wherein said cage body has a shape selected from the group consisting of a quadrangular shape.

* * * * *